US006219674B1

(12) United States Patent
Classen (10) Patent No.: US 6,219,674 B1
(45) Date of Patent: Apr. 17, 2001

(54) SYSTEM FOR CREATING AND MANAGING PROPRIETARY PRODUCT DATA

(75) Inventor: John Barthelow Classen, Baltimore, MD (US)

(73) Assignee: Classen Immunotherapies, Inc., Baltimore, MD (US)

( * ) Notice: Subject to any disclaimer, the term of this patent is extended or adjusted under 35 U.S.C. 154(b) by 0 days.

(21) Appl. No.: 09/449,178

(22) Filed: Nov. 24, 1999

(51) Int. Cl.[7] .................................................. G06F 17/00
(52) U.S. Cl. ............................. 707/104; 707/100; 705/2; 705/3; 600/300
(58) Field of Search ........................... 705/2, 3; 600/300; 707/104, 100; 435/5

(56) References Cited

U.S. PATENT DOCUMENTS

| 5,642,731 | * | 7/1997 | Kehr ...................................... 600/300 |
| 5,737,539 | | 4/1998 | Edelson et al. . |
| 5,833,599 | | 11/1998 | Schrier et al. . |
| 5,845,255 | | 12/1998 | Mayaud . |
| 5,876,926 | * | 3/1999 | Beecham .................................... 435/5 |
| 5,908,383 | | 6/1999 | Brynjestad . |
| 5,970,463 | * | 10/1999 | Cave et al. ................................. 705/3 |
| 6,000,828 | * | 12/1999 | Leet ...................................... 600/300 |

OTHER PUBLICATIONS

Chen et al., "Vaccine Safety Datalink Project: A New Tool for Improving Vaccine Safety Monitoring in the United States", *Pediatrics,* vol. 99, No. 6, (Jun. 1997).
DeStefano et al., "Timing of Hepatitis B Vaccination and Risk of Insulin–Dependent Diabetes Mellites", *Pharmacoepidemiology and Drug Safety,* vol. 6: Supplement 2 (1997).

* cited by examiner

*Primary Examiner*—Wayne Amsbury
*Assistant Examiner*—Thuy Pardo
(74) *Attorney, Agent, or Firm*—Evelyn H. McConathy; Dilworth Paxson LLP (57) ABSTRACT

Systems and methods for creating and using product data to enhance the safety of a medical or non-medical products. The systems receive vast amounts of data regarding adverse events associated with a particular product and analyze the data in light of already known adverse events associated with the product. The system develops at least one proprietary database of newly discovered adverse event information and new uses for the product and may catalog adverse event information for a large number of population subgroups. The system may also be programmed to incorporate the information into intellectual property and contract documents. Manufacturers can include the information in consumer product information which they provide to consumers or, in the case of certain medical products, prescribers of the medical products.

75 Claims, 6 Drawing Sheets

SYSTEM FOR CREATING AND MANAGING PROPRIETARY PRODUCT DATA

FIELD OF THE INVENTION

The present invention relates in general to computer systems and databases for managing product data. More particularly, the invention employs computer systems and proprietary databases for gathering, storing, processing and distributing adverse events data associated with medical and non-medical products.

BACKGROUND OF THE INVENTION

For several reasons, adverse events associated with medical and non-medical products are greatly understated. As a matter of cost, thorough safety studies are typically very expensive to conduct. In the field of generic pharmaceuticals, for example, the cost of doing safety testing is prohibitive because a manufacturer's survival in the business is based on being a low cost producer. By the time a product becomes generic, its safety information has already been generated and shared. Thus, manufacturers that did not fund the original safety studies enjoy the benefits of the information without incurring the costs thereof and have no economic motivation to conduct additional studies.

Manufacturers also have little incentive to identify adverse events related to their products. As the number and/or type of identified adverse events increases with respect to a particular product, the product becomes less attractive to consumers and the manufacturer's exposure to potential product liability litigation increases.

Safety studies to receive marketing approval for medical and related products such as drugs, biologicals, medical devices and cosmetics generally involve relatively small populations of individuals (typically a few thousand or less) observed for short periods of time in prospective randomized studies. The studies generally involve strict inclusion criteria and persons in the study often differ in many respects from persons taking the drug post-marketing. The differences between the safety studies participants and post-marketing consumers may include age, sex, race, preexisting medical conditions, and use of other drugs or devices. Pre-marketing safety studies are therefore a less than desirable means of identifying the full array of potentially adverse product events in the general and specific post-marketing consumers populations.

Post-marketing safety studies normally involve voluntary reporting of potential adverse events. However, there is often no way to be certain that these occurrences are caused by the medical product or not. For instance, adverse events generally are reported if they occur within a short time of initiating treatment with a product. It is difficult for a clinician to link an adverse event to a medical product if it occurs months after starting or even discontinuing use of the product.

Additionally, when a potential adverse event is something that frequently occurs in people who do not use the medical product it is difficult to determine if the medical product increases the frequency and/or magnitude of the event. This scenario is problematic because the incidence of such events in a matched control population is often not known. Under these circumstances, it cannot be readily discerned whether the incidence of adverse events is greater in the group using the medical product versus a corresponding control population. Therefore, since the rate or intensity of adverse events associated with use of a product cannot be accurately determined, a reliable assessment of whether the risk of using a product exceeds the product's benefit cannot be made.

Pre-marketing and post-marketing of medical products is regulated by the Food and Drug Administration (FDA) and manufacturers are required to disclose all adverse events caused by their products. Nevertheless, in the pharmaceutical industry very few truly comprehensive and detailed studies on adverse events are conducted. Most studies are performed by contract research organizations funded by pharmaceutical companies as part of required FDA safety studies. A few government funded studies are also performed. Both of these sorts of studies generally do not detect frequency of adverse events in specific subgroups as defined by typical demographic factors like age, sex, etc. The adverse events data from these studies is made free to the public, including competing product manufacturers, and the FDA. Such limited data has resulted in misused and underdeveloped sectors of the pharmaceutical industry. That is, some products continue to be prescribed when they should not be while other products are not prescribed when they should be. In either case, unnecessary adverse events and patient suffering may occur. Accordingly, the consumer cost of improperly prescribed medical products is needlessly high since a manufacturer's cost to produce a medical product includes manufacturing costs and costs arising from adverse events. For example, some vaccine manufacturers are responsible for compensating individuals who develop unforeseen vaccine adverse events.

Proper product labeling discourages those at high risk from utilizing the product thus decreasing adverse events and, ultimately, the consumer cost of the product. Some factors affecting high risk use include drug dosing and drug combinations. Proper labeling of adverse events associated with these and other high risk factors reduces the number of adverse events, thereby decreasing a manufacturer's product liability exposure and consumer product cost. To date, however, there has been no realization of the potential for comprehensive, subscriber-accessible proprietary product safety information to enhance the quality and reliability of adverse event reporting and product labeling.

U.S. Pat. Nos. 5,737,539, 5,833,599 5,845,255 and 5,908,383 disclose computerized systems for providing patient-specific medical treatment information. The systems enable health care providers such as medical doctors to access databases containing pharmacological or other medical information via a computer and match a patient's medical symptoms and/or prescription history with known data to produce an appropriate prescription or treatment for the patient. These systems do not analyze raw adverse event data or create proprietary adverse event information based on such data that may be used to identify new uses or restrictions for medical products or to develop improved packaging information that can accompany medical products.

As described by Robert T. Chen, M.D., et al. in "Vaccine Safety Datalink Project: A New Tool for Improving Vaccine Safety Monitoring in the United States" published in Pediatrics, Vol.99, No. 6, June 1997, computers have also been used to verify previously reported adverse events related to vaccines. The so-called VSD project discussed therein promotes utilizing its research in the development and use of safer vaccines. However, it does not disclose the notion of identifying new and proprietary uses for existing vaccines based on the discovery of new adverse events associated with the vaccines. Moreover, the VSD project cannot discern new adverse events from previously reported adverse events.

An advantage exists, therefore, for a system for analyzing adverse event data associated with medical and non-medical products and for creating useful proprietary adverse event information based on the analyzed adverse event data. The adverse event information may be used, for example, to identify new uses or restrictions for medical or non-medical products or to develop improved packaging information that can accompany medical or non-medical products. Particular benefits arising from the use of such a system would be in connection with products already on the market because of the potentially extensive pre-existing data for the products that may be analyzed for adverse events.

SUMMARY OF THE INVENTION

The present invention utilizes a computerized system for gathering, storing and processing adverse event data associated with medical and non-medical products to create proprietary databases containing useful adverse event information. The adverse event information may be used, for example, to identify new uses or restrictions for medical or non-medical products or to develop improved packaging information that can accompany medical or non-medical products.

In certain preferred embodiments, the system gathers, stores and analyzes vast amounts of adverse event data from patients being treated by a particular medical product. The system can be used to track essentially unlimited product data. The useful adverse event information contained in the proprietary databases may include, for example, catalogs of previously known and newly identified adverse events associated with the product. The proprietary databases may be subscriber-accessible for direct release to any persons or entities having a need or desire for the information including, without limitation, consumers, manufacturers, research institutions, health care providers, regulatory agencies and attorneys. The system preferably also has the capability to format the adverse event information for incorporation into licensing contract documents that may be used in negotiations with product manufacturers. The manufacturers, in turn, may use the information to develop and market new uses for existing products. The information may also be used by the manufacturers to provide improved packaging information that can accompany their products to inform consumers or medical product prescribers of new uses for their medical products. New uses may comprise restrictive uses coupled with directions or warnings not to use the product in certain populations or situations where the system according to the invention identifies the risk of adverse events as being increased. Other new uses may include more expansive uses of the product. For example, the new use could be coupled with directions to promote more frequent use of the product in certain populations or situations relative to other populations or situations. In either case, a kit can be produced containing the product and improved warning, instructions and/or labeling.

Although not limited thereto, the present invention is especially useful in reducing unforeseen adverse events caused by medical products including, but not limited to, drugs, vaccines, nonvaccine biologicals and medical devices. When the medical product is a drug, the product may be proprietary (e.g., protected by patent) or generic. In varying degree, generics of a proprietary drug differ from the proprietary drug and from one another. More particularly, although their active ingredients may be the same, generic drugs may include impurities, inert substances, carriers and other agents that may not be present in their corresponding proprietary drugs or other generic alternatives thereof. When considering generics and their proprietary counterparts based solely on their active ingredients, the generics would be expected to exhibit similar adverse events. However, through implementation of the present invention, generic drugs can be precisely compared against their proprietary drugs and alternative generics to determine the impact of their inactive ingredients on adverse events despite the variability of such inactive ingredients. For instance, drugs with agents which delay the release of an active agent can be expected to exhibit many of the same side effects as drugs with the same active ingredient but that release it over a shorter period of time. In this context, therefore, a generic and a proprietary drug may be considered to be the same product if the adverse event(s) and/or new use(s) for the drugs would be expected to be similar for both.

For non-drug medical products such as biological products and medical products, as well as non-medical products, similar products having similar characteristics can be adjudged similarly for their adverse event information. For instance, if the a red truck and a black truck would be considered the same product if they are equipped with the same or similar fuel tanks and their risk of fuel tank explosions is based on the design of the fuel tank.

Other details, objects and advantages of the present invention will become apparent as the following description of the presently preferred embodiments and presently preferred methods of practicing the invention proceeds.

BRIEF DESCRIPTION OF THE DRAWINGS

The invention will become more readily apparent from the following description of preferred embodiments thereof shown, by way of example only, in the accompanying drawings wherein.

DETAILED DESCRIPTION OF THE INVENTION

Figure 1:
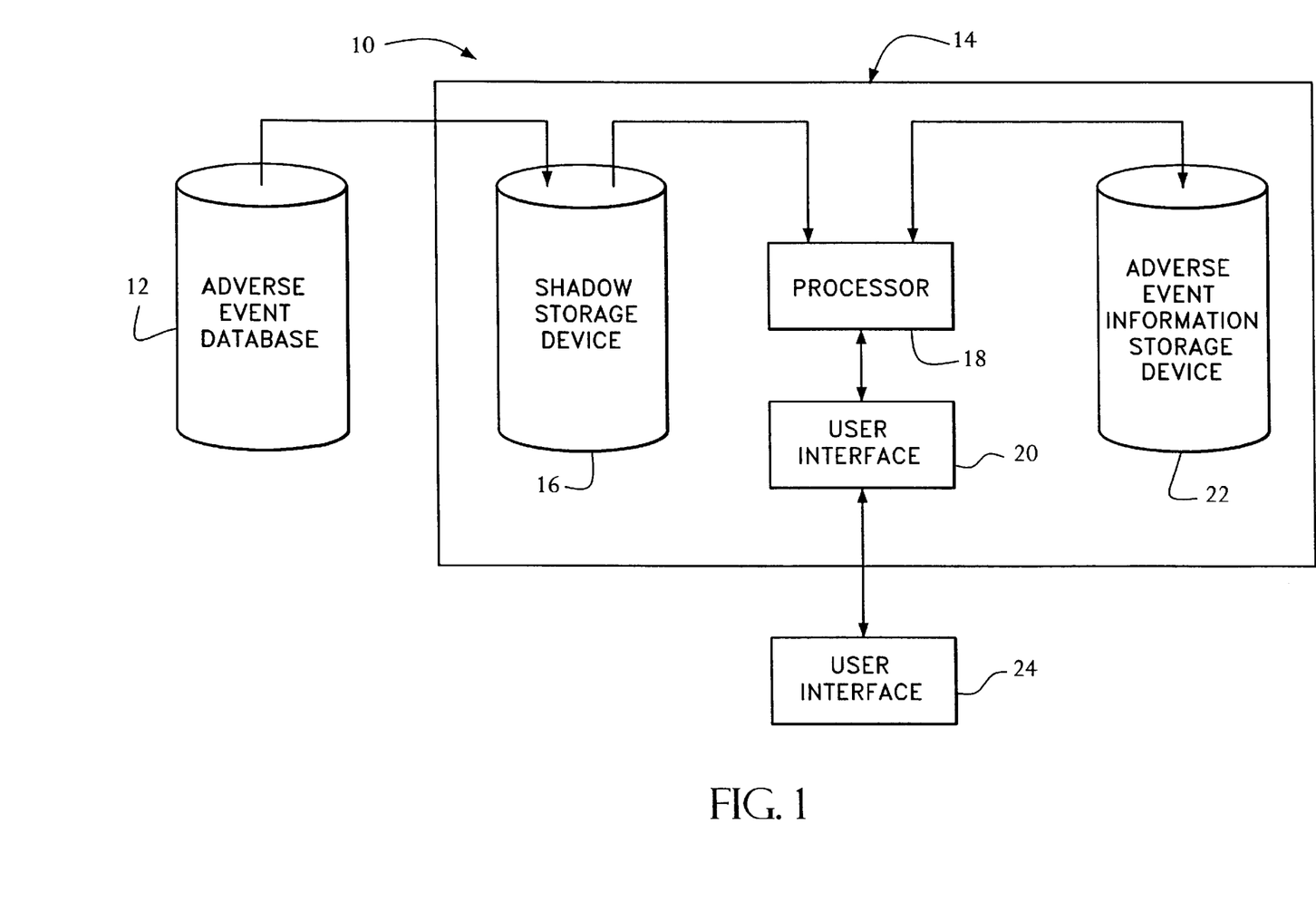
FIG. 1 is a schematic view of a first embodiment of a system according to the present invention.

Referring to the drawings wherein like references indicate like elements throughout the several views, there is shown in FIG. 1 a first system 10 constructed in accordance with the present invention. System 10 includes at least one adverse event database 12 and a server 14. Depending upon their source, the adverse event database(s) 12 may be accessed by server 14 free of charge or for a fee. Adverse event database 12 preferably contain large amounts of data regarding a particular medical or non-medical product.

The term "medical product" as used herein shall be construed to mean drugs, vaccines, nonvaccine biologicals, medical devices and any other medically-related goods and therapies. Drugs and biologicals can represent any known class of drugs. These can be categorized by their effects on an organ system such as cardiac, respiratory, renal etc. Drugs and biologicals can also be classified by their chemical composition, e.g., sulfa drugs, penicillin derivatives, antibodies, etc. In addition, they can be classified according to their activity, e.g., diuretic, antibiotic, beta blocker, etc.

Medical devices can be similarly classified by those of ordinary skill in the art, e.g., medical devices may be grouped as defibrillators, EKG machines, infusion pumps, CT machines, etc. To further assist in the categorization process, those skilled in the art may consult medical science resources such as medical libraries or online authorities such as MEDLINE® and the like to locate articles, books or other printed or electronic publications on the subject of interest such as the non-limiting example of Goodman and Gilman's "The Pharmacological Basis of Therapuetics". "Non-medical product" shall be construed to mean any non-medically-related product that may cause harm to a consumer including, without limitation, foods, food additives, beverages, vitamins, alcohol, tobacco, cosmetics, mechanical devices and children's toys, personal and household cleaning products, and other chemicals such as paints and related coatings, insecticides, herbicides and industrial chemicals.

Because of the large volume of data that they contain, preferred adverse event databases may include those of medical insurance companies, managed care organizations, pharmaceutical and medical device manufacturers, public health departments, hospitals and the like. Typically, each adverse event recorded in such databases links the adverse event with demographic information such as the age, sex and race and, frequently, one or more physical condition factors of the individual that experienced the adverse event. The result is that adverse event database 12 may contain thousands or even millions of items of data. Such vast repositories of information enable the data to be analyzed to generate statistically relevant and reliable information relating to age, gender, racial, physical condition or other subgroup.

Server 14 preferably includes a shadow storage device 16, a processor 18, a user interface 20 and an adverse event information storage device 22. Shadow storage device 16 gathers and stores adverse event data received from the adverse event database(s) 12. Processor 18 may be any computer processing means suitable for executing the operations of the present method as described hereinafter. User interface 20 may include any suitable input/output (I/O) equipment. Adverse event information storage device 22 stores adverse event information that is generated by processor 18 responsive to analysis of the adverse event data stored in shadow storage device 16. The shadow and adverse event information storage devices 16, 22 may be any memory devices capable of storing large amounts of information. Lastly, system 10 includes a user computer 24 for interfacing with user interface 20. User computer 24 is preferably any commercially available personal computer, workstation or the like which can exchange information with user interface 20 in the manner well known in the art.

In the event data relating to a medical product is desired, the adverse event data in adverse event database 12 can be collected using the ICD and other disease codes on admission, discharge, pharmaceutical sales, physician visit records or other known sources. The systems of the present invention may also accommodate and process animal safety test data such as animal toxicity data.

Through operation of system 10 and the other systems described herein, the data extracted from the adverse event database 12 is analyzed by suitable programming of processor 18 to produce useful adverse event information that is storable in adverse event information storage device 22. For example, the adverse event database may store information on frequency of adverse events such as death, hospitalization, office visits, disability, missed work, medical costs, abnormal lab results and surgeries in individuals receiving the medical product in question and this information can be compared to the observed adverse event rate in the same persons before receiving the medical product or in persons of similar characteristics (i.e., a control group). The analysis can be performed on different exposure rates including but not limited to the amount, duration and timing of exposure to the product.

Additional adverse event information may also be derived from subgroup analysis. Subgroup analysis can be performed to determine specific high risk groups who may be at increased risk of having an adverse event. Subgroups can include persons with similar characteristics such as sex, age, race, weight, height, percent body fat, genetic characteristics, pregnancy status, allergies, additional medical problems, use of additional medical products (including devices), past medical history, family history, social history, occupation, use of alcohol, tobacco, recreational drugs, and history of abnormal lab tests such as EKG, chest x-ray, liver function test and kidney function test. The subgroup analysis can include groups that were not represented or were underrepresented in safety studies that were required for marketing approval or were done around the time of market introduction. For example, a drug may be approved for use in persons over the age of 18. However, people under 18 may also receive the drug. In such case, packaging for the drug may not include sufficient warnings for persons under 18, in general, and subgroups of persons under 18, in particular, that are at greater risk of adverse events linked to usage of the product.

Ideally, systems according to the invention can track large numbers of variables to locate groups at high risk of adverse events. As a non-limiting example, the systems could be configured to track people taking multiple different drugs to determine whether a toxic adverse event occurs in people taking all of the drugs at once. The systems may utilize statistical formulae to identify groups at high or low risk of adverse events.

The systems according to the invention may also optionally collect and analyze efficacy data. The benefit of the medical product in certain subgroups can thus be measured by observing the frequency of the intended benefit, (e.g., decreased death, stroke, kidney failure, and so on). Benefits can also include reductions in costs where the costs may include, without limitation, costs of the medical product, medical expenses and lost productivity. By using the data from the risks and benefits one can determine the risk/benefit for persons in any particular subgroup. This information can be highly stratified to enable, in addition to previously known uses, new, different or more precise uses for a product. For example, a dose of a drug or biologic, the frequency or manner of use of a device, or the setting of a device such as a pacemaker may be precisely prescribed to accommodate the individual needs of particular subgroups.

Targeted searches can be performed and their data analyzed by the systems of the present invention. For example, if it is discovered from one adverse event database 12 that persons receiving a medical product are at increased risk of dying of liver failure at a certain dose of medication or when taking the drug in combination with other drugs, then one can attempt to verify the findings using a second adverse event database 12. Adverse event data from either adverse event data can also be confirmed in animals or by prospective clinical trials in humans. Targeted searches can also be done after case reports of adverse reactions, discovery of adverse events in animals, adverse events discovered in similar products and possible adverse found in small studies.

Consistent with the invention, any number or variety of proprietary databases may be storable on adverse event information storage device 22. For instance, a first proprietary database can be created containing information about a particular product's adverse events and, optionally, risk benefits and cost benefits of the product. The data from that database can be crossed, linked or compared with a database of knowledge already accumulated on the product that may also be stored on adverse event information storage device 22. Sources of prior known adverse events can include package inserts, the Physician's Desk Reference, The Merck Manual, data from regulatory agencies such as the FDA, and published literature found on databases such as MED-LINE®. New findings on adverse reactions can thus be determined through appropriate comparison and/or interpretation of the databases. The newly derived knowledge can include, without limitation, catalogs of new adverse events, specific frequency of adverse events, drug interactions and side effects in specific subgroups such as those mentioned above. For instance, a new adverse event can mean a newly discovered adverse reaction such as the discovery of an increased rate of seizures associated with a drug, improved information such as more accurate calculation of the rates of seizures in a group or subgroup, or the discovery of an increased rate of seizures in patients taking the drug along with one or more additional drugs.

Figure 2:
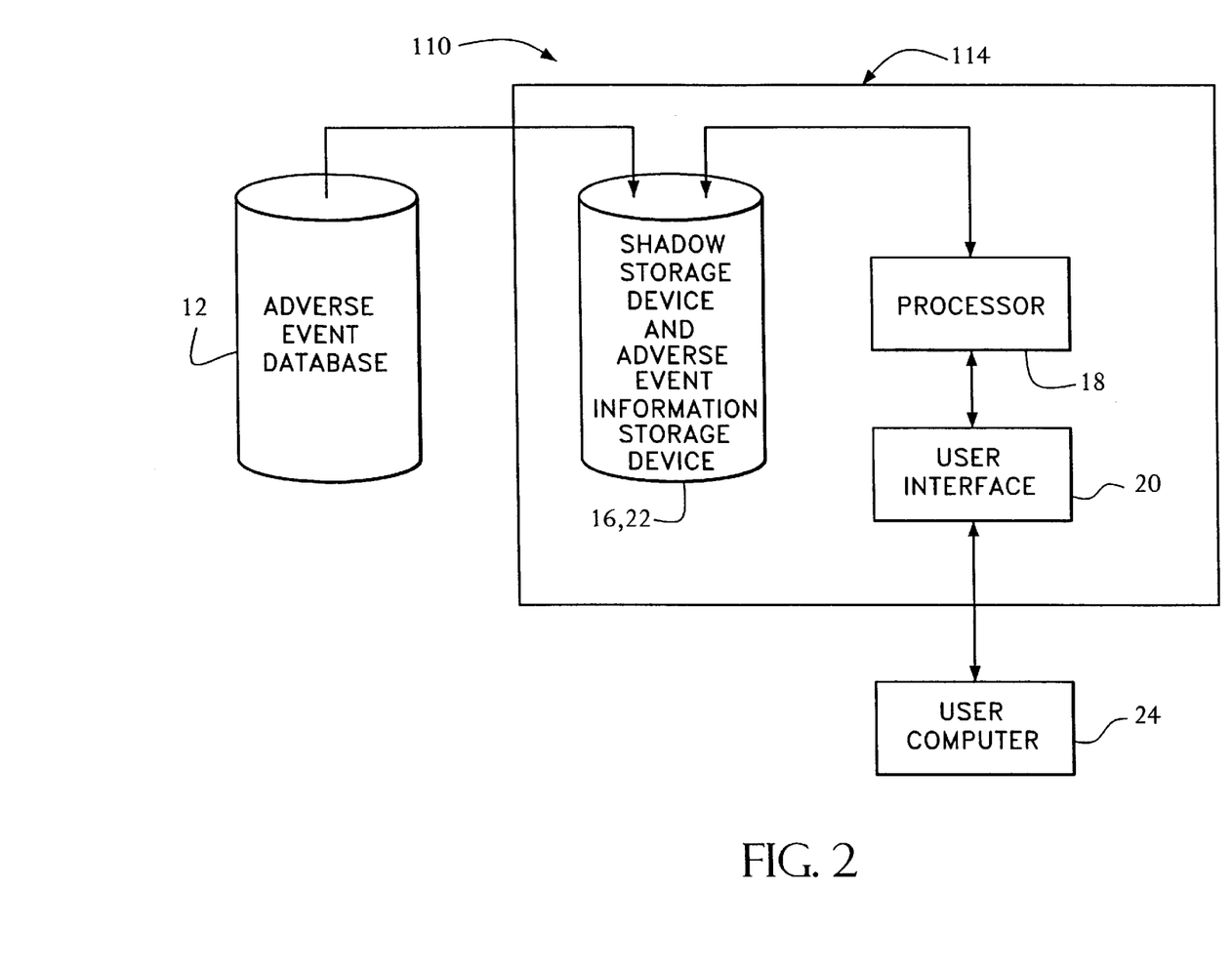
FIG. 2 is a schematic view of a further embodiment of a system according to the present invention.

FIG. 2 represents a further preferred embodiment of a system according to the invention identified by reference numeral 110. System 110 is constructed and functions substantially similarly to system 10 of FIG. 1 with the exception being that the shadow storage device 16 and adverse event information storage device 22 of system 10 are integrated into a single shadow storage device and adverse event information storage device 16, 22 on server 114.

Figure 3:
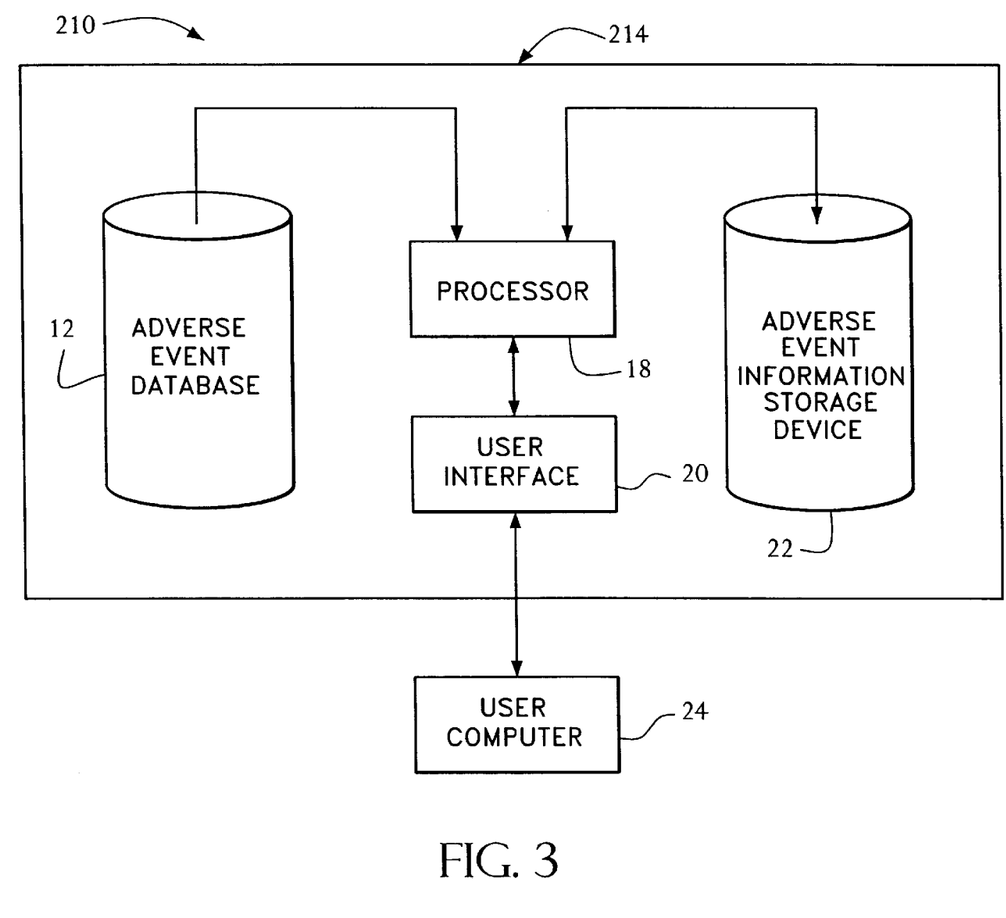
FIG. 3 is a schematic view of a further embodiment of a system according to the present invention.

FIG. 3 represents a further preferred embodiment of a system according to the invention identified by reference numeral 210. System 110 also is constructed and functions substantially similarly to system 10 of FIG. 1. However, unlike systems 10 and 110, system 210 draws its raw adverse event data from an internal rather than an external source. That is, server 214 of system 210 directly supports adverse event database(s) 12. System 210 graphically depicts a situation wherein a holder of a substantial body of adverse event data may itself analyze such data using processor 18 and create one or more adverse event information databases that may be stored on adverse event information storage device 22. Exemplary users of system 210 may include, for example, medical insurance companies, managed care organizations, pharmaceutical and medical device manufacturers, public health departments, hospitals and the like. Although illustrated as separated devices, it is also contemplated that adverse event database(s) 12 and adverse event information storage device 22 may be integrated into a single storage device.

Figure 4:
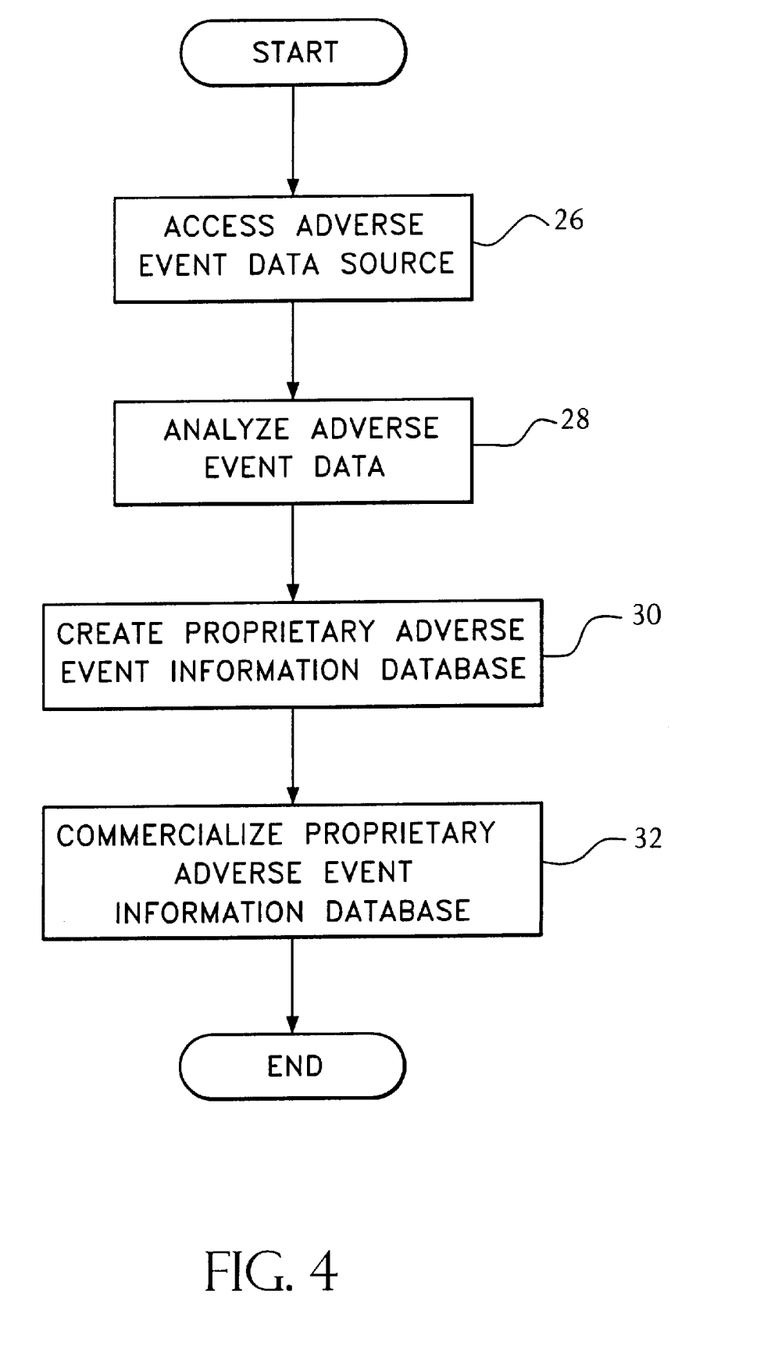
FIG. 4 is a flow chart illustrating the method according to the present invention.

FIG. 4 is a flow chart that embodies the essential method steps of the present invention that are executed by each of systems 10, 110 and 210. At step 26, the adverse event database(s) 12 are accessed by server 10, 110 or 210 (at a fee or free of charge) to obtain desired adverse event data therefrom. In systems 10 and 110, the adverse event database(s) 12 are external to the servers 14 and 114. Hence, servers 14 and 114 desirably store the data received from databases 12 in shadow storage devices 16. Server 214, by contrast, accesses its internal adverse event database(s) 12 for the desired data.

The desired adverse event data having been accessed, the processor 18 of systems 10, 110 and 210 then analyzes the data, as described above, to identify previously known and new adverse events, as indicated at step 28. At step 30, the processor 18 further processes the analyzed adverse event data to create useful proprietary adverse event information such as any of the kinds mentioned above. More particularly, in creating the proprietary adverse event information database at step 30, processor 18 preferably possesses logic whereby it categorizes the newly-discovered adverse event (s) associated with a particular product that are identified at step 28 and also identifies at least one new use for the product responsive to the identification of at least one new adverse event(s) associated with the product. The processor 18 then stores the adverse event information as one or more databases in adverse event information storage device 22.

According to presently preferred embodiments of the invention, the data retrieved from adverse event database(s) 12 is processed and analyzed by a centralized processor 18 on server 14, 114 or 214 and the analyzed data is stored at an adverse event information storage device also supported by server 14, 114 or 214. Alternatively, the proprietors of servers 14, 114 or 214 may license proprietary software to users of user computers 24 that may perform the functions of processor 18. Such software may be loaded onto the user computers 24 to execute the adverse event data analyzing and other processing functions of processor 18 described above and the generated useful adverse event information may be stored at the user computers 24. In any case, servers 14, 114 and 214 can be directly connected by a user interface 24 such as a modem. It will be understood that the servers 14, 114 and 214 may also be indirectly connected to user computers 24 via one or more other servers, a central computer or other system designed to link computers or other processing machines. Ideally the information should be transferred digitally between servers 14, 114 and 214 and user computers 24. Alternatively, however, it can be transmitted in analog form by a modem along standard telephone lines. It will be further understood that the information can also be transferred by disk, printed and then scanned in or, alternatively, manually rekeyed. Preferably, the user computers 24 and their associated printers (not illustrated) are sufficiently sophisticated to organize and print all information generated by the systems 10, 110 and 210 in virtually any desired format and on essentially any desired printable medium that may be printed by the printers. However, certain product labels and package inserts that incorporate the information can be manually type faced using typesetting or other conventional printing techniques. The system may also format the data for submission to regulatory agencies such as the FDA.

The proprietary information that may be generated by the systems of the present invention is superior in many ways to the limited and generally static adverse event data and databases heretofore known in the art. In respect to medical products in particular, the volume of data and the degree to which the data may be stratified and studied, the systems according to the invention far exceed the capabilities of FDA-required pre-marketing studies for medical products. To illustrate, a typical FDA pre-marketing study generally involves study populations of less than about 5000 and normally less than about 2000 participants. In contrast, the adverse event data that may be amassed and analyzed pursuant to the invention may contains involve information on far larger numbers of people receiving the medical product. Representative populations studied using the present system in virtually all practical medical product scenarios will be at least 5000 and can be anlayzed in any desired increment such as, for example, 5,000; 10,000; 50,000; 100,000; 200,000; 1 million or more.

The systems of the present invention will additionally provide a better appreciation of delayed or latent adverse events caused by medical products long after initiation of treatment or after treatment has been discontinued. Using the present systems, post-exposure follow-up of a product can be analyzed in any desired increments of time. For instance, selected post-exposure study periods may be as brief as a few minutes or hours to considerably lengthier periods such as 1 day, 2 days, 7 days, 10 days, 30 days, 90 days, 180 days, 1 year, 3 years, 5 years, 10 years or more.

Risk/benefit analyses may also be readily performed using the methods and systems described herein. Acceptable adverse event thresholds may be established and studied for a product. The adverse event thresholds may be selected to be at any desired incidence level, e.g., 1:10,000,000; 1:1,000,000; 1:100,000; 1:10,000; 1:1,000; 1:100, above which use of a product may exceed its benefit for a general or specific population group. The adverse event thresholds serve as limits for single or aggregated newly discovered adverse events. For example, an adverse event threshold of 1 occurrence in 1000 persons may be established as an acceptable level of occurrences. If 2 occurrences are observed in the target population then the adverse event threshold is exceeded and the product is deemed unsafe or commercially impractical for use by persons in that group. Likewise, 10 new similar or dissimilar adverse events relating to the product may be observed in the target group, but none of the individual new adverse events occurs more than once in 10,000 persons. In the aggregate, therefore, the 10 occurrences detected in a total study population of 10,000 persons corresponds to a ratio of 1:1000 which equals but does not exceed the acceptable adverse event threshold for the product under scrutiny. In this instance, the product would be deemed safe and commercially viable for use in the targeted population group.

The present systems and methods also enable ready comparisons between target populations that receive treatment with a product and experience adverse events and untreated control groups that experience similar adverse events. For example, a target group treated with a certain vaccine that acquires diabetes may be compared with an otherwise identical but unvaccinated control group that also acquires diabetes. Increased incidences of diabetes in the target group thus may be attributable to the vaccine. Systems 10, 110 and 210 may programmed to establish any desired acceptable increased rates of adverse event occurrences in the treated target group versus the untreated control group, e.g., 2%, 5%, 10%, 20%, 30%, 50%, 75%, 100%, 150%, 200%, 300%, 400%, 600%, 800%, 1,000% or more, above which treatment would be contraindicated in the target group. Preferably, the system can analyze data using any desired study design. For example, a case control study design may be used where the frequency of using a product in a group with the target disease is compared to the frequency of using a product in a group of controls. The studies may include prospective clinical trials and retrospective follow-up of clinical trials, as well as cohort analysis of people not in clinical trials. The studies may or may not include efficacy for the intended use as in treatment of a specific disease. The studies may also be part of a pre-approval or post-marketing study regulated by the FDA or similar regulatory body. Conversely, the studies may be unaffiliated with FDA-sanctioned clinical trials.

Returning to FIG. 4, the adverse event information stored in adverse event information storage device 22 is commercialized. Commercialization of the useful adverse event information may take on an assortment of forms as indicated in FIGS. 5 and 6.

Users of servers 10, 110 and 210 may include individual, a corporation, partnership, government agencies, research institutions or any other persons or entities that may have an interest in or need for new and useful adverse event information. Non-limiting examples include manufacturers of medical products, insurance companies, health maintenance organizations and public health departments. In the case of manufacturers of medical products, such manufacturers may use the information in the manufacture of their own products or may license the information to their competitors. As indicated by step 26' in FIGS. 5 and 6, at the request any of these persons or entities or on its own behalf, the owner or licensee of server, 14, 114 or 214 accesses and retrieves raw adverse event product data from adverse event database(s) 12. At step 28' the server analyzes the retrieved data to identify new adverse events regarding a product, to conduct cost/benefit analyses related to the newly discovered adverse events or to perform any other desired analysis of the raw data. At step 30' the server creates one or more proprietary adverse information databases that are stored in adverse information storage device 22. At step 32' in FIG. 5 the licensee or owner or owner of server 14, 114 or 214 commercializes the adverse event information in adverse information storage device 22 by selling or licensing the proprietary information to a third party. The third party communicates with system 10, 110 or 210 through user computer 24. The user computer interfaces with user interface 20 to make requests for information to and to receive information from the processor 18 of server 14, 114 or 214. Interpretation of the received information may be performed by the third party, an independent contractor, the owners or licensees of server 14, 114 or 214 or the owner(s) or licensees of the adverse event database(s) 12.

Figure 5:
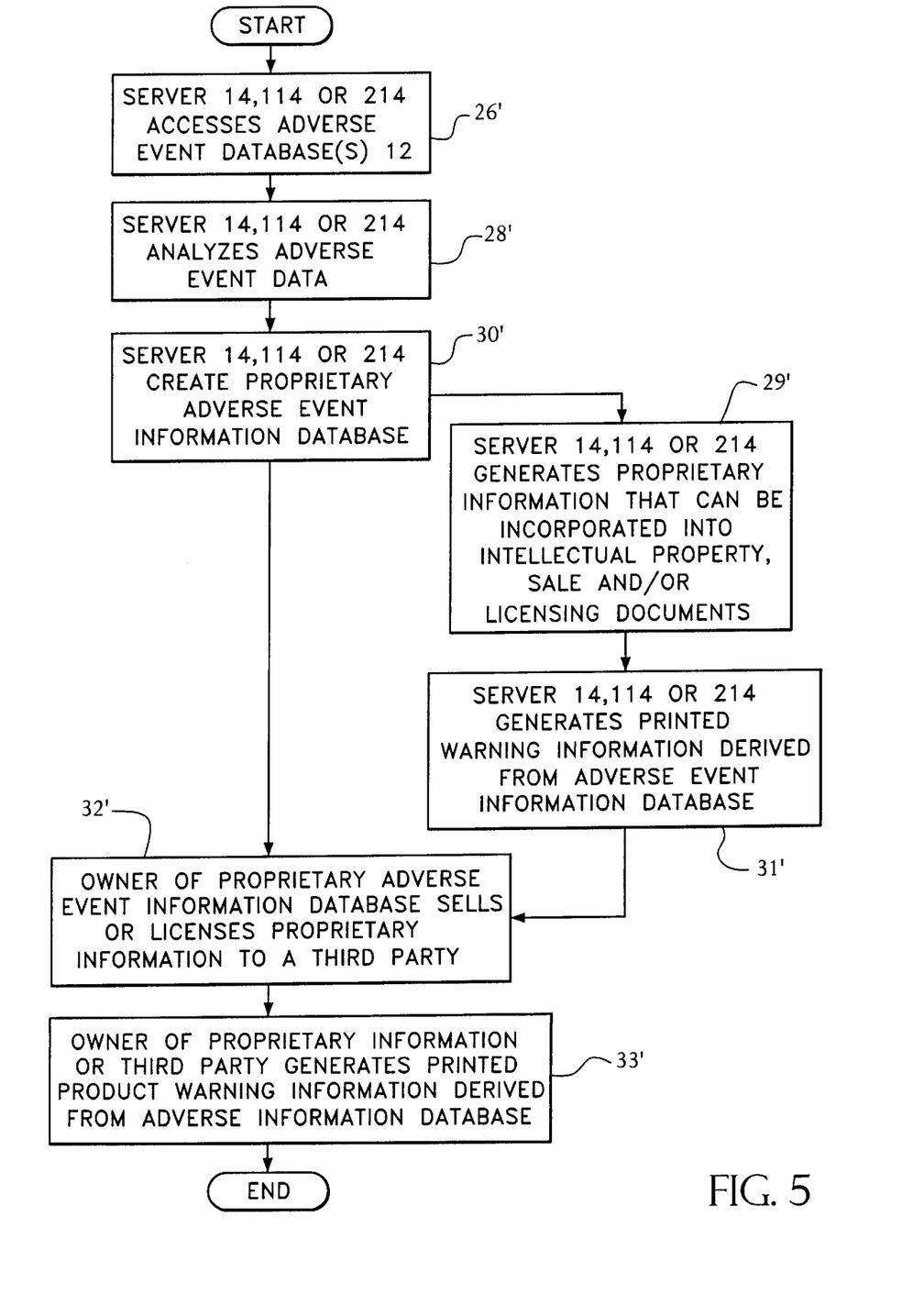
FIG. 5 is a first preferred specific application of the method represented in FIG. 4.

Practical but non-limiting examples of possible users of systems 10, 110 or 210 and the method depicted in FIG. 5 include manufacturers of medical products, holding companies, venture capital companies or other companies or individuals seeking to capitalize on ownership of a portfolio of new medical product information that may be of commercial value. The users may use the information to seek patent, copyright or other intellectual property protection for the information. The systems 10, 110 and 210 and the methods depicted in FIGS. 5 and 6 are especially useful for creating proprietary information and products. As used herein, proprietary information shall be construed to mean information that is used or intended to be used for establishing or claiming specific intellectual property rights. For example, the proprietary information can be used in the creation of intellectual property, sale or licensing documents. That is, the proprietary information may comprise textual or graphical content that may be incorporated into patent or copyright applications. Users might seek patent protection for new therapeutic uses for existing products based on newly discovered adverse event information. Similarly, users might seek copyright protection for new labeling necessitated by the discovery of the new adverse event information. For any new use discovered by the systems according to the present invention, the instructions accompanying the product for which the new use is identified should desirably warn newly-identified high risk users of the product to avoid using the product. Likewise, the instructions should also inform users who were previously but wrongly identified as high risk users that the product may be safely used by them. Preferably, systems 10, 110 and 210 are capable of formatting the proprietary information data such that it is suitable for incorporation into the aforementioned intellectual property documents.

Figure 6:
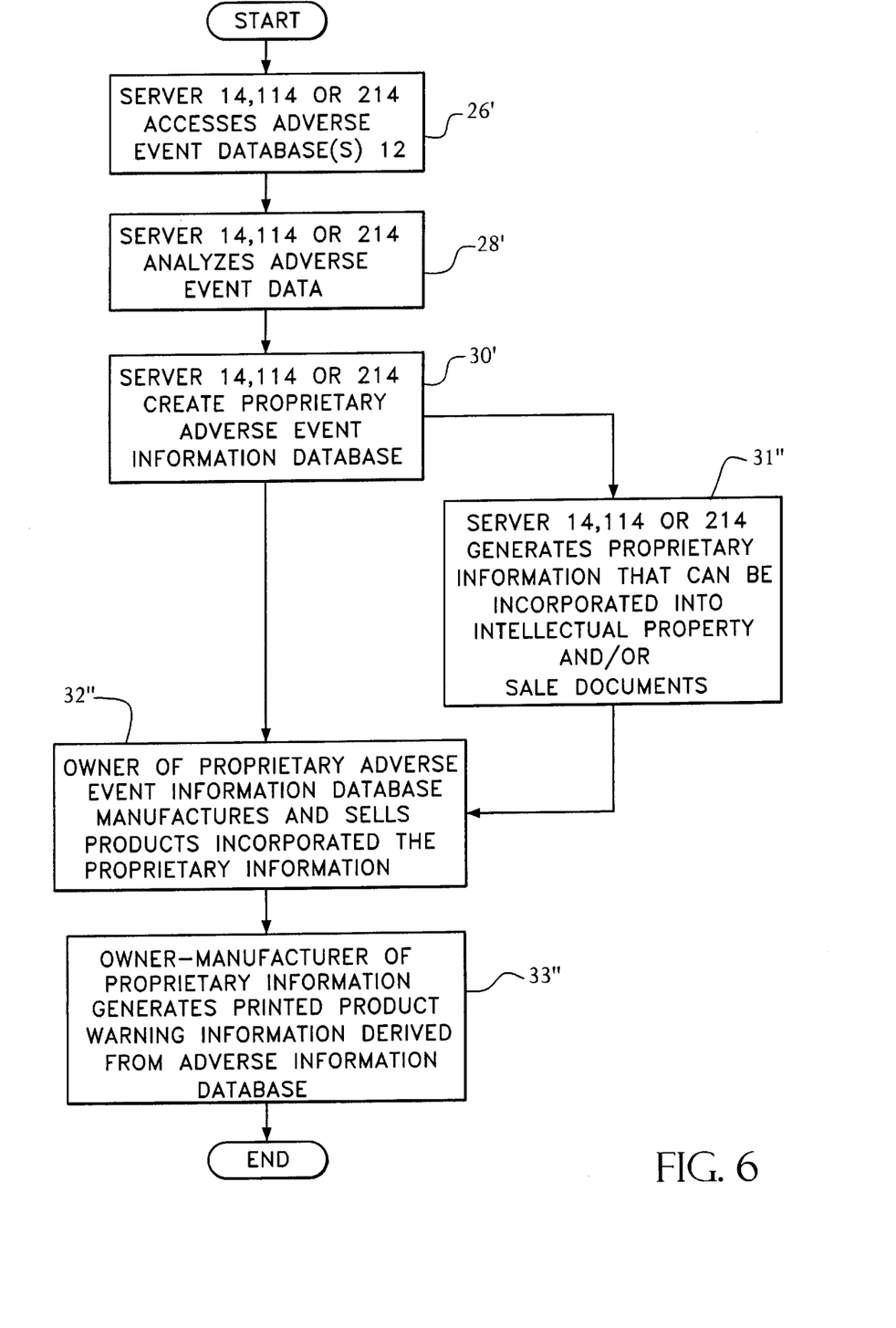
FIG. 6 is a further preferred specific application of the method represented in FIG. 4.

In FIG. 6, method steps 26', 28' and 30' are identical to their counterparts in FIG. 5. However, as indicated at step 32" of FIG. 6, the owner or user of the proprietary adverse information commercializes the proprietary information by manufacturing (or causing to be manufactured) products incorporating the proprietary information and then selling the products.

In addition to the functions represented by method steps 26', 28', 30', 32' and 32", additional tasks are preferably performed to more completely fulfil the purposes of the present invention as reflected in FIGS. 5 and 6. For example, as indicated by step 29' in FIG. 5, server 14, 114 or 214 may be programmed to generate proprietary information, typically in textual and/or graphic form, that can be incorporated into intellectual property, sale and/or licensing documents. The documents then can be used in negotiations with product manufacturers or other interested third parties. Additionally, FIG. 5 reveals in step 31' that server 14, 114 or 214 may optionally generate printed product warning information derived from the adverse information database(s). The printed warning information may be used in connection with product packaging such as, for example, as product labeling or as product packaging inserts to advise the consumer (or product prescriber in the case of medical products requiring a prescription) of contraindications or other adverse events associated with use of the product. Alternatively, as shown in step 33' of FIG. 5, the owner of the proprietary information or its licensee may generate the aforesaid printed warning information.

Similarly, in FIG. 6, the server 14, 114 or 214 may generate proprietary information that may be incorporated into intellectual property and/or sale documents (step 31"). Printed product warning information may also be generated by the servers 14, 114 or 214. Alternatively, as shown at step 33", this step may be performed by the owner or licensee of the proprietary information (who also manufactures the product or causes it to be manufactured).

Equipped with the new adverse information generated by systems 10, 110 and 210, a user might also urge the FDA to compel existing manufacturers of a product to remove the product from the market if it does not have adequate safety warnings or to prevent those contemplating marketing the product from entering the market without providing adequate safety labeling.

In a preferred application, the systems described herein may be used to develop new proprietary safer uses for drugs that are already generic or soon to become generic (i.e., whose patents will soon expire). These drugs may have been on the market for ten or more years and little research may have been conducted before or during that time to identify and optimize the fullest extent of their potential ranges of safe use.

Many entities, large and small, may beneficially utilize the systems described herein, A representative, although non-limiting, example would be an independent non-manufacturing company that procures access to one or more adverse event databases to analyze the data contained therein and identify new uses for existing drugs. The independent company could then license the "new use" technology it discovers to pharmaceutical manufacturers. The content of the licensing agreements may be agreed upon before or after the data has been analyzed. The independent company may opt to file appropriate intellectual property documents such as patent or copyright applications covering the newly-discovered uses for the product and/or their attendant product warning information and receive monies derived from the sale of the drug in the form of royalties or a lump sum fee. Alternatively, the independent company may utilize the services of a contract manufacturer that will make the drug for the independent company which will reserve the right to sell the product on its own behalf. The independent company may also be a large medical insurer or pharmaceutical company that has access to its own extensive adverse event information database(s) from which may identify and commercially exploit new uses for existing medical products.

As mentioned above, the present systems and methods can also be utilized to develop proprietary safety information on products unrelated to the medical fields since manufacturers in other fields of endeavor generally are required to provide consumers with safety information regarding their products.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

Any description of a class or range as being useful or preferred in the practice of the invention shall be deemed a description of any subclass or subrange contained therein, as well as a separate description of each individual member or value in said class or range.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A system for creating and using product data comprising:
   at least one adverse event database for storing adverse event data associated with a commercially available product;
   a processor for accessing and analyzing data from said at least one adverse event database to assist in identifying new adverse events associated with the product and to assist in identifying at least one new use for the product responsive to identification of at least one new adverse event associated with the product;

an adverse event information storage device for storing at least new adverse event data identified by said processor;

a user computer for making requests for adverse event information to and for receiving adverse event information from said processor;

a user interface for interfacing said processor and said user computer.

2. The system of claim 1 wherein said processor, said adverse event information storage device and said user interface reside on a server.

3. The system of claim 2 wherein said at least one adverse event database resides on said server.

4. The system of claim 2 wherein said at least one adverse event database does not reside on said server.

5. The system of claim 4 further comprising a shadow storage device for storing adverse event data associated with a product that is retrieved from said at least one adverse event database.

6. The system of claim 5 wherein said shadow storage device resides on said server.

7. The system of claim 1 wherein said adverse event information storage device additionally stores previously known adverse event data associated with the product.

8. The system of claim 1 wherein the product is a medical product.

9. The system of claim 8 wherein the medical product is a generic drug.

10. The system of claim 1 wherein the product is a non-medical product.

11. The system of claim 1 wherein said product data is proprietary.

12. A proprietary product created using the system of claim 1.

13. A proprietary kit containing the product and labeling notifying a user of at least one new adverse event for the product, the kit being created using the system of claim 1.

14. A method of using the proprietary kit of claim 13 in accordance with a proprietary new use for a commercially available product.

15. A method for creating and using product data, said method comprising the steps of:

accessing at least one adverse event data source that stores adverse event data associated with a commercially available product;

analyzing said adverse event data to identify new adverse events associated with the product;

creating at least one adverse event information database, said creating comprising analyzing data from said at least one adverse event data source to identify at least one new use for the product responsive to identification of at least one new adverse event associated with the product, said creating further comprising storing adverse event information, said adverse event information including said at least one new use; and commercializing adverse event information stored at said at least one adverse event information database.

16. The method of claim 15 further comprising creating sale or licensing documents incorporating said adverse event information stored at said at least one an adverse event database.

17. The method of claim 15 further comprising generating printed product warning information derived from said adverse event information stored at said at least one an adverse event database.

18. The method of claim 15 wherein said step of generating printed product warning information is performed by a server which supports operation of said method.

19. The method of claim 15 wherein said step of generating printed product warning information is performed by a third party purchaser or third party licensee that purchases or licenses said adverse event information from an owner of said adverse event information.

20. The method of claim 15 wherein said step of commercializing comprises selling or leasing of said adverse event information.

21. The method of claim 15 wherein said step of commercializing comprises manufacturing and selling products incorporating said adverse event information.

22. The method of claim 15 further comprising creating intellectual property, sale or licensing documents incorporating information from said at least one adverse event information database.

23. The method of claim 22 wherein said intellectual property documents comprise patent applications.

24. The method of claim 22 wherein said intellectual property documents comprise copyright applications.

25. The method of claim 15 wherein said at least one an adverse event information database additionally stores previously known adverse event data associated with the product.

26. The method of claim 15 wherein said at least one adverse event data source stores adverse event data in populations of at least about 5000 persons.

27. The method of claim 15 wherein said at least one an adverse event information database additionally stores post-exposure adverse event product data in selected time increments ranging from less than one hour to more than ten years.

28. The method of claim 15 wherein said at least one an adverse event information database additionally stores risk versus benefit information regarding new adverse event data associated with the product.

29. The method of claim 15 wherein said at least one an adverse event information database additionally stores comparative adverse event data for target groups receiving the product and control groups not receiving the product.

30. The method of claim 15 wherein the product is a medical product.

31. The method of claim 30 wherein the medical product is a generic drug.

32. The method of claim 15 wherein the product is a non-medical product.

33. The method of claim 15 wherein said product data is proprietary.

34. The method of claim 15 wherein said at least one new use is a restrictive use restricting use of said product in at least one population group observed in said creating step to be at high risk of adverse events associated with use of the product.

35. The method of claim 15 wherein said at least one new use is an expansive use expanding use of said product in at least one population group observed in said creating step to be at low risk of adverse events associated with use of the product.

36. The method of claim 15 further comprising conducting at least one prospective study to verify a newly discovered adverse event.

37. The method of claim 15 wherein said adverse event information further comprises information on at least one of a user's sex, weight, age, race, genetic characteristics, medical condition, pregnancy status, allergies, use of medicines and use of medical devices.

38. The method of claim 15 wherein said adverse event information further comprises information on amount or duration of exposure by a user to the product.

39. The method of claim 15 wherein said adverse event information database further stores information on at least one adverse event including death, hospitalization, missed work, medical costs, abnormal lab results and surgeries.

40. The method of claim 15 wherein said adverse event information database further stores information including rates of adverse events occurring in population ratios as frequently as 1:100 up to about 1:10,000,000.

41. The method of claim 15 wherein said adverse event information database further stores information on cumulative adverse events.

42. The method of claim 15 wherein said adverse event information database further stores information with the interaction of a plurality different products.

43. The method of claim 15 wherein said at least one adverse event data source comprise a plurality of adverse event data sources.

44. A proprietary product created using the method of claim 15.

45. A proprietary kit containing the product and labeling notifying a user of at least one new adverse event for the product, the kit being created using the method of claim 15.

46. A method of using the proprietary kit of claim 45 in accordance with a proprietary new use for a commercially available product.

47. A method of establishing at least one new use for a commercially available product, said method comprising the steps of:
comparing raw adverse event data associated with a product with previously known adverse event data associated with the product;
observing in said raw adverse event data at least one new adverse event associated with the product; and
identifying at least one new use for the product responsive to observing said at least one new adverse event associated with the product.

48. The method of claim 47 further comprising generating printed product warning information containing notification of said new adverse event data associated with the product.

49. The method of claim 48 further comprising providing said printed product warning information in connection with product packaging.

50. The method of claim 48 wherein the product is a medical product.

51. The method of claim 50 wherein the medical product is a generic drug.

52. The method of claim 47 wherein the product is a non-medical product.

53. The method of claim 47 wherein said at least one new use is proprietary.

54. The method of claim 47 wherein said at least one new use is a restrictive use restricting use of said product in at least one population group observed in said creating step to be at high risk of adverse events associated with use of the product.

55. The method of claim 47 wherein said at least one new use is an expansive use expanding use of said product in at least one population group observed in said creating step to be at low risk of adverse events associated with use of the product.

56. The method of claim 47 further comprising conducting at least one prospective study to verify a newly discovered adverse event.

57. The method of claim 47 wherein said adverse event information further comprises information on at least one of a user's sex, weight, age, race, genetic characteristics, medical condition, pregnancy status, allergies, use of medicines and use of medical devices.

58. The method of claim 47 wherein at least one of said raw adverse event data and said previously known adverse event data is stored on at least one computerized database.

59. A proprietary product created using the method of claim 47.

60. A proprietary kit containing the product and labeling notifying a user of at least one new adverse event for the product, the kit being created using the method of claim 47.

61. A method of using the proprietary kit of claim 60 in accordance with a proprietary new use for a commercially available product.

62. A computer for managing product data comprising:
at least one database storing adverse event data associated with a commercially available product;
a processor for accessing and analyzing data from said at least one database to assist in identifying new adverse events associated with the product and assist in identifying at least one new use for the product responsive to identification of at least one new adverse event associated with the product; and
an adverse event information storage device for storing adverse event information including said at least one new adverse event associated with the product and said at least one new use for the product identified by said processor.

63. The computer of claim 62 further comprising a user interface for interfacing said processor with a user computer.

64. The computer of claim 62 wherein said at least one adverse event database resides on said computer.

65. The computer of claim 62 wherein said at least one adverse event database does not reside on said computer.

66. The computer of claim 65 further comprising a shadow storage device for storing adverse event data associated with the product that is retrieved from said at least one adverse event database.

67. The computer of claim 66 wherein said shadow storage device resides on said server.

68. The computer of claim 62 wherein said adverse event information storage device additionally stores previously known adverse event data associated with the product.

69. The computer of claim 62 wherein the product is a medical product.

70. The computer of claim 69 wherein the medical product is a generic drug.

71. The computer of claim 62 wherein the product is a non-medical product.

72. The computer of claim 62 wherein said product data is proprietary.

73. A proprietary product created using the computer of claim 62.

74. A proprietary kit containing the product and labeling notifying a user of at least one new adverse event for the product, the kit being created using the computer of claim 62.

75. A method of using the proprietary kit of claim 74 in accordance with a proprietary new use for a commercially available product.

* * * * *

(12) EX PARTE REEXAMINATION CERTIFICATE (9607th)
United States Patent
Classen (10) Number: US 6,219,674 C1
(45) Certificate Issued: Apr. 23, 2013

(54) SYSTEM FOR CREATING AND MANAGING PROPRIETARY PRODUCT DATA

(75) Inventor: John Barthelow Classen, Baltimore, MD (US)

(73) Assignee: Classen Immunotherapies, Inc., Baltimore, MD (US)

Reexamination Request:
No. 90/007,638, Jul. 22, 2005

Reexamination Certificate for:
Patent No.: 6,219,674
Issued: Apr. 17, 2001
Appl. No.: 09/449,178
Filed: Nov. 24, 1999

(51) Int. Cl.
*G06F 19/326* (2006.01)
*G06F 19/328* (2006.01)
*G06F 19/363* (2006.01)
*G06Q 50/22* (2006.01)
*G06Q 50/24* (2006.01)

(52) U.S. Cl.
USPC ............... 707/770; 600/300; 600/705; 600/2; 600/707; 600/999.1; 600/999.104; 600/999.107

(58) Field of Classification Search .................. 705/2, 3; 707/104.1, 300, 100
See application file for complete search history.

(56) References Cited

To view the complete listing of prior art documents cited during the proceeding for Reexamination Control Number 90/007,638, please refer to the USPTO's public Patent Application Information Retrieval (PAIR) system under the Display References tab.

*Primary Examiner* — Majid A. Banankhah (57) ABSTRACT

Systems and methods for creating and using product data to enhance the safety of a medical or non-medical products. The systems receive vast amounts of data regarding adverse events associated with a particular product and analyze the data in light of already known adverse events associated with the product. The system develops at least one proprietary database of newly discovered adverse event information and new uses for the product and may catalog adverse event information for a large number of population subgroups. The system may also be programmed to incorporate the information into intellectual property and contract documents. Manufacturers can include the information in consumer product information which they provide to consumers or, in the case of certain medical products, prescribers of the medical products.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-75 are cancelled.

* * * * *